United States Patent [19]
Kadokura et al.

[11] Patent Number: 6,046,345
[45] Date of Patent: Apr. 4, 2000

[54] BARIUM STRONTIUM β-DIKETONATES, PROCESSES FOR PRODUCING THE SAME AND PROCESSES FOR PRODUCING BARIUM STRONTIUM-CONTAINING OXIDE DIELECTRIC FILMS WITH THE USE OF THE SAME

[75] Inventors: Hidekimi Kadokura, Tokyo; Yumie Okuhara, Sakado, both of Japan

[73] Assignee: Kabushikikaisha Kojundokagaku Kenkyusho, Saitama, Japan

[21] Appl. No.: 09/252,046

[22] Filed: Feb. 17, 1999

[30] Foreign Application Priority Data

Apr. 17, 1998 [JP] Japan ................... 10-144998

[51] Int. Cl.[7] .................. C07F 3/00; C23C 16/06
[52] U.S. Cl. .................... 556/1; 556/28; 427/255.32
[58] Field of Search ............ 556/28, 1; 427/255.32

[56] References Cited

PUBLICATIONS

Schwarberg et al., Analytical Chemistry, vol. 42, No. 14, pp. 1828–1830, Dec. 1970.

*Primary Examiner*—Porfirio Nazario-Gonzalez
*Attorney, Agent, or Firm*—Fattibene & Fattibene; Paul A. Fattibene; Arthur T. Fattibene

[57] ABSTRACT

Novel one-source compounds for producing $(Ba,Sr)TiO_3$ films having high dielectric constants and ferroelectric $(Sr,Ba)Nb_2O_6$ films by the CVD method, which are in the form of a liquid at the source temperature and contain Ba and Sr at a specified ratio; processes for producing these novel compounds; and processes for producing films by using the same.

Because of having a melting point of 160° C., being in the form of a liquid and having enough vapor pressure at 200° C., the novel compounds barium strontium β-diketonate $[Ba_2Sr(dpm)_6$ and $BaSr_2(dpm)_6]$ can be quantitatively supplied by gas bubbling as a feedstock in the CVD method while maintaining the Ba/Sr ratio at a constant ratio. Thus, barium strontium-containing oxide dielectric films can be produced at a high reproducibility by thermal decomposition on a substrate in an oxidative atmosphere. These compounds can be produced by reacting dpmh with Ba and Sr, $Ba(dpm)_2$ with $Sr(dpm)_2$, or dpmH with Ba and $Sr(dpm)_2$ and then subjecting either of the reaction products thus obtained to high-vacuum distillation.

5 Claims, 4 Drawing Sheets

BARIUM STRONTIUM β-DIKETONATES, PROCESSES FOR PRODUCING THE SAME AND PROCESSES FOR PRODUCING BARIUM STRONTIUM-CONTAINING OXIDE DIELECTRIC FILMS WITH THE USE OF THE SAME

BACKGROUND OF THE INVENTION

1. Field of the Invention

This invention relates to barium strontium β-diketonates, processes for producing the same and processes for producing barium strontium-containing oxide dielectric films by the chemical vapor deposition method (hereinafter referred to simply as the CVD method) with the use of the same.

2. Description of the Prior Art

Investigations are in progress on $(Ba,Sr)TiO_3$ films (hereinafter referred to simply as BST films) having high dielectric constants and ferroelectric $(Sr,Ba)Nb_2O_6$ films (hereinafter referred to simply as SBN films) as DRAM capacitors usable in the generation of gigabit techniques and the CVD method excellent in mass productivity and step coverage properties is highly expected to be useful in forming these films. However, these films are three-component systems, which makes it difficult to regulate the compositional ratio Ba:Sr:Ti. This difficulty is partly caused by the fact that there has been known no Ba and Sr compounds usable as a CVD feedstock which is in the form of a liquid being excellent in the controllability in supply, has a sufficient vapor pressure and shows a high heat stability at the source temperature.

At the present time, investigations are in progress mainly on barium β-diketonates, in particular, barium bis (dipivaloylmethanate) [hereinafter referred to simply as $Ba(dpm)_2$] as the barium compound, and strontium β-diketonates, in particular, strontium bis (dipivaloylmethanate) [hereinafter referred to simply as $Sr(dpm)_2$] as the strontium compound. These compounds have melting points in the range of 200 to 220° C. and vapor pressures at 200° C. of about 0.01 Torr.

It is much convenient to control the supply system from two sources compared with the case of the supply from three sources. Although the source number can be lessened by using as one source a single compound containing both of two components Ba and Sr, no such compound has been known hitherto. It is anticipated that a metal β-diketonate composed of two different elements might be formed as in the case of a double alkoxide formed from two metal alkoxides of different elements which are liable to undergo association with each other. However, there has never been reported in public so far that such a molecule is formed. J. E. Schwarberg, R. E. Sievers and R. W. Moshier [Anal. Chem., 42, 1828 (1970)] reported that when a mixture of $Ca(dpm)_2$ with $Sr(dpm)_2$ was subjected to gas chromatography at 250° C., only one peak was observed and this peak showed a retention time different from those of $Ca(dpm)_2$ and $Sr(dpm)_2$ chromatographed individually; that thus $Ca(dpm)_2$ could not be separated from $Sr(dpm)_2$ by gas chromatography; and $CaSr(dpm)_3^+$ was observed in the mass spectrum of a fraction obtained by melting $Ca(dpm)_2$ together with $Sr(dpm)_2$ and recovering by evaporation. Based on these facts, they estimated that $Ca(dpm)_2$ would react with $Sr(dpm)_2$ in the course of the gas chromatography to thereby form a composite complex $CaSr(dpm)_4$ with a heterogenous elemental nucleus.

$[Ca(dpm)_2]_2 + [Sr(dpm)_2]_2 = 2CaSr(dpm)_4$.

However, the identification of $CaSr(dpm)_4$ and measurement of its physical properties are insufficient and still at the level of estimation. As a matter of course, no description on $(Ba,Sr)_1(dpm)_2$ is given therein.

SUMMARY OF THE INVENTION

One of the problems to be solved by the present invention is to disclose novel one-source compounds each containing Ba and Sr at a specified ratio and being useful as a substitute for two-source compounds composed of a Ba compound and a Sr compound in the formation of BST films or SBN films by the CVD method. Still another problem is to provide processes for producing these novel compounds. Still another problem is to provide processes for producing barium strontium-containing oxide dielectric films by the CVD method with the use of these novel compounds.

DESCRIPTION OF THE PREFERRED EMBODIMENTS

The present inventors have conducted for a long time studies on the synthesis of organometallic compounds and the CVD method with the use of the same. To solve the problems as described above, they first individually synthesized $Ba(dpm)_2$ and $Sr(dpm)_2$ compounds. Then each compound was subjected to high-vacuum distillation and the melting point and vapor pressure thereof were measured. The vapor pressure was measured by the gas saturation method wherein porous ceramic particles were impregnated with the compound in a molten state to thereby support the compound on the particles. Next, $Sr(dpm)_2$ and Ba were reacted with dipivaloylmethane (hereinafter referred to simply as dmpH) to give a molar ratio of $Ba(dpm)_2$ to $Sr(dpm)_2$ of 1:1, followed by high-vacuum distillation to recover the distillate in three fractions, i.e., the first, second and third fractions (Example 1). The melting point of each fraction was measured and the composition [Ba, Sr, (dpm)] thereof was analyzed. Further, the evaporation properties were examined by TG-DTA. As a result, it was found out that the obtained product was highly favorable as a CVD feedstock. The results of the FD-MS (field desorption-mass spectroscopy) analysis on these fractions as the molecular species indicated that the obtained product was not a mere mixture but a novel compound mainly comprising $(Ba,Sr)_3(dpm)_6$ [including $Ba_2Sr(dpm)_6$ and $BaSr_2(dpm)_6$].

Starting with the novel compound in the form of a liquid at 200° C., an attempt has been made to form BST films. That is, a carrier gas is bubbled thereinto and thus the (Ba,Sr) component is supplied into a CVD apparatus. As a result, it has been found out that excellent films can be obtained constantly thereby. The present invention has been thus completed. Therefore, the present invention has made it possible to produce the novel compound $(Ba,Sr)_3(dpm)_6$ which contains as a single source the (Ba,Sr) component for producing barium strontium-containing oxide dielectric films by the CVD method and can be supplied in the form of a liquid.

The novel compounds according to the present invention are barium strontium β-diketonates, namely, β-disketonates containing at least one barium atom and at least one strontium atom in the molecule formed by association.

Examples of the β-diketonates are listed in Table 1.

TABLE 1

| Abbreviation | Chemical Formula | Name |
| --- | --- | --- |
| thd or dpm | —$C_{11}H_{19}O_2$ | 2,2,6,6-tetramethyl-3,5-heptanedionate (commonly called "dipivaloylmethanate") |
| tod | —$C_{11}H_{19}O_2$ | 2,2,7-trimethyl-3,5-octanedionate |
| tmhpd | —$C_{10}H_{17}O_2$ | 2,2,6-trimethyl-3,5-heptanedionate |
| dmhpd or dim | —$C_9H_{15}O_2$ | 2,6-dimethyl-3,5-heptanedionate (commonly called "diisobutyryl methanate") |
|  | —$C_9H_{15}O_2$ | 2,2-dimethyl-3,5-heptanedionate |
| tmod | —$C_{12}H_{21}O_2$ | 2,2,6,6-tetramethyl-3,5-octanedionate |

Next, the most commonly employed dpm system will be described by way of example.

Figure 1:
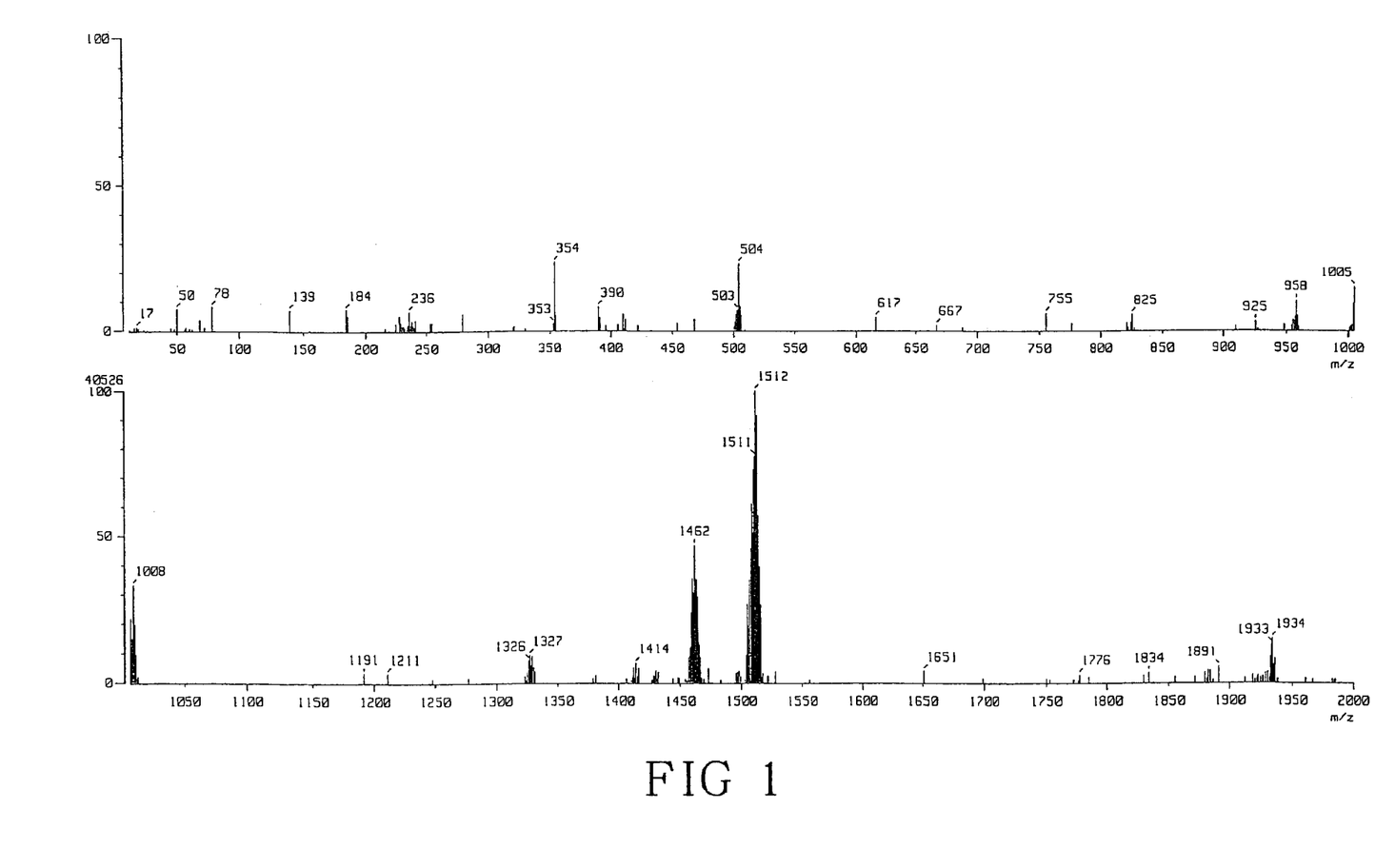
FIG. 1 shows the FD-MS chart of Ba $(dpm)_2$, more particularly, $(Ba_{0.999}Sr_{0.001})(dpm)_2$.

The $Ba(dpm)_2$ and $Sr(dpm)_2$ synthesized by the present inventors by reacting dipivaloylmethane with barium or strontium followed by high-vacuum distillation existed as trimers, i.e., $Ba_3(dpm)_6$ and $Sr_3(dpm)_6$ in benzene solution, as well as in vapor phase according to the results of the FD-MS analysis (cf. FIG.1).

The results of the identification of a product corresponding to $(Ba,Sr)_1(dpm)_2$, which has an atomic ratio of Ba:Sr of about 1 and is produced by the production process according to the present invention and the method as will be described in Example 1, will be now described.

In conclusion, this product was not a mixture of $Ba_3(dpm)_6$ with $Sr_3(dpm)_6$ but a mixture of a novel compound $Ba_2Sr(dpm)_6$ with another novel compound $BaSr_2(dpm)_6$.

Now, the identification will be described in detail.
Procedure for the Identification of the Product Corresponding to $(Ba,Sr)_1(dpm)_2$ Having an Atomic Ratio of Ba:Sr of about 1

The product was subjected to high-vacuum simple distillation at 0.02 Torr and the distillate was divided into the first, second and third fractions. In this case, little still residue was observed.

Two samples were taken from each fraction and the Ba and Sr contents were analyzed. Table 2 shows the results.

TABLE 2

Analytical data on the composition of high-vacuum simple distillation fraction

| Fraction (wt. %) | Sample | Ba (wt. %) | Sr (wt. %) | dpm (wt. %)* | Atomic ratio Ba:Sr | Molar ratio dpm/(Ba + sr) |
| --- | --- | --- | --- | --- | --- | --- |
| 1st (32) | 1 | 13.6 | 9.36 | 77.0 | 0.480:0.520 | 2.04 |
|  | 2 | 13.6 | 9.51 | 76.9 | 0.477:0.523 | 2.02 |
| 2nd (36) | 1 | 14.0 | 9.75 | 76.3 | 0.478:0.522 | 1.95 |
|  | 2 | 13.8 | 9.68 | 76.5 | 0.476:0.524 | 1.98 |
| 3rd (32) | 1 | 14.1 | 9.53 | 76.4 | 0.486:0.514 | 1.97 |
|  | 2 | 14.2 | 9.50 | 76.3 | 0.488:0.512 | 1.97 |
| Average |  |  |  |  | 0.481:0.519 | 1.99 |

*calculated by taking dpm(wt. %) as 100 − (Ba + Sr).

As Table 2 shows, the compositions of the all fractions agreed with each other within the scope of analytical errors, which suggests that the composition of the product was the same throughout the evaporation.

Next, the molecular weight of each fraction was determined by the cryoscopic method with the use of benzene.

TABLE 3

Results on the molecular weight determination of high-vacuum simple distillation fraction

| Fraction | Sample (g) | Benzene (g) | ΔT (° C.) | M.w. |
| --- | --- | --- | --- | --- |
| 1st | 1.3403 | 19.9 | 0.264 | 1310 |
| 2nd | 1.6691 | 20.1 | 0.263 | 1610 |
| 3rd | 1.2138 | 20.2 | 0.197 | 1560 |

Although the data were somewhat scattered, the molecular weights ranged from 1,300 to 1,600. The molecular weights of the estimated trimers are as follows:
$Ba_3(dpm)_6$: 1512
$Ba_2Sr(dpm)_6$: 1462
$BaSr_2(dpm)_6$: 1412
$Sr_3(dpm)_6$: 1362.

Thus, the product was highly likely one composed of these compounds.

Next, molecular species were measured to determine whether the above fractions were a mere mixture of the known compound $Ba_3(dpm)_6$ with another known compound $Sr_3(dpm)_6$ or a mixture of a novel compound $Ba_2Sr(dpm)_6$ with another novel compound $BaSr_2(dpm)_6$, etc. The FD-MS analysis was employed in the measurement.

In electron impact-MS (EI-MS) or chemical ionization-MS (CI-MS), it is sometimes observed that only small molecular ion peaks or even no peak can be observed due to the occurrence of a number of fragment ions. In contrast thereto, the FD-MS analysis employed herein has an advantage that molecular ion peaks can be easily observed.

Instrument MS: JEOL SX-102.

Ionization method: FD ion polarity: + emitter: carbon emitter current: 0–40 mA.

Measurement conditions accelerating voltage: 8 kV range: m/z=0–2000 scanning speed: 15 sec/decade.

Sample and Result:

The FD-MS data of $Ba(dpm)_2$, more particularly, $(Ba_{0.999}Sr_{0.001})(dpm)_2$ are shown in FIG. 1.

Figure 2:
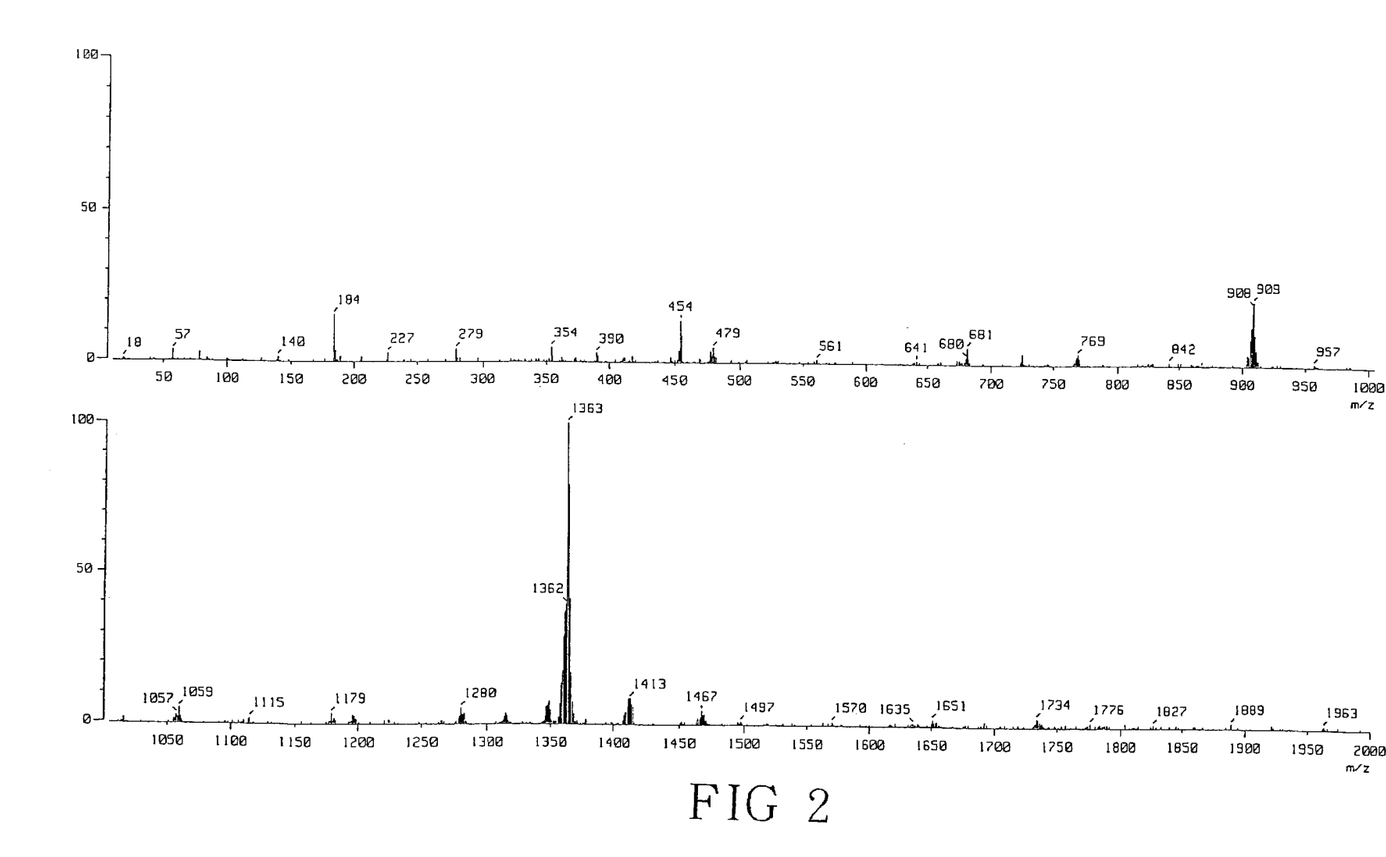
FIG. 2 shows the FD-MS chart of $Sr(dpm)_2$, more particularly, $(Ba_{0.003}Sr_{0.997})(dpm)_2$.

The FD-MS data of $Sr(dpm)_2$, more particularly, $(Ba_{0.003}Sr_{0.997})(dpm)_2$ are shown in FIG. 2.

Figure 3:
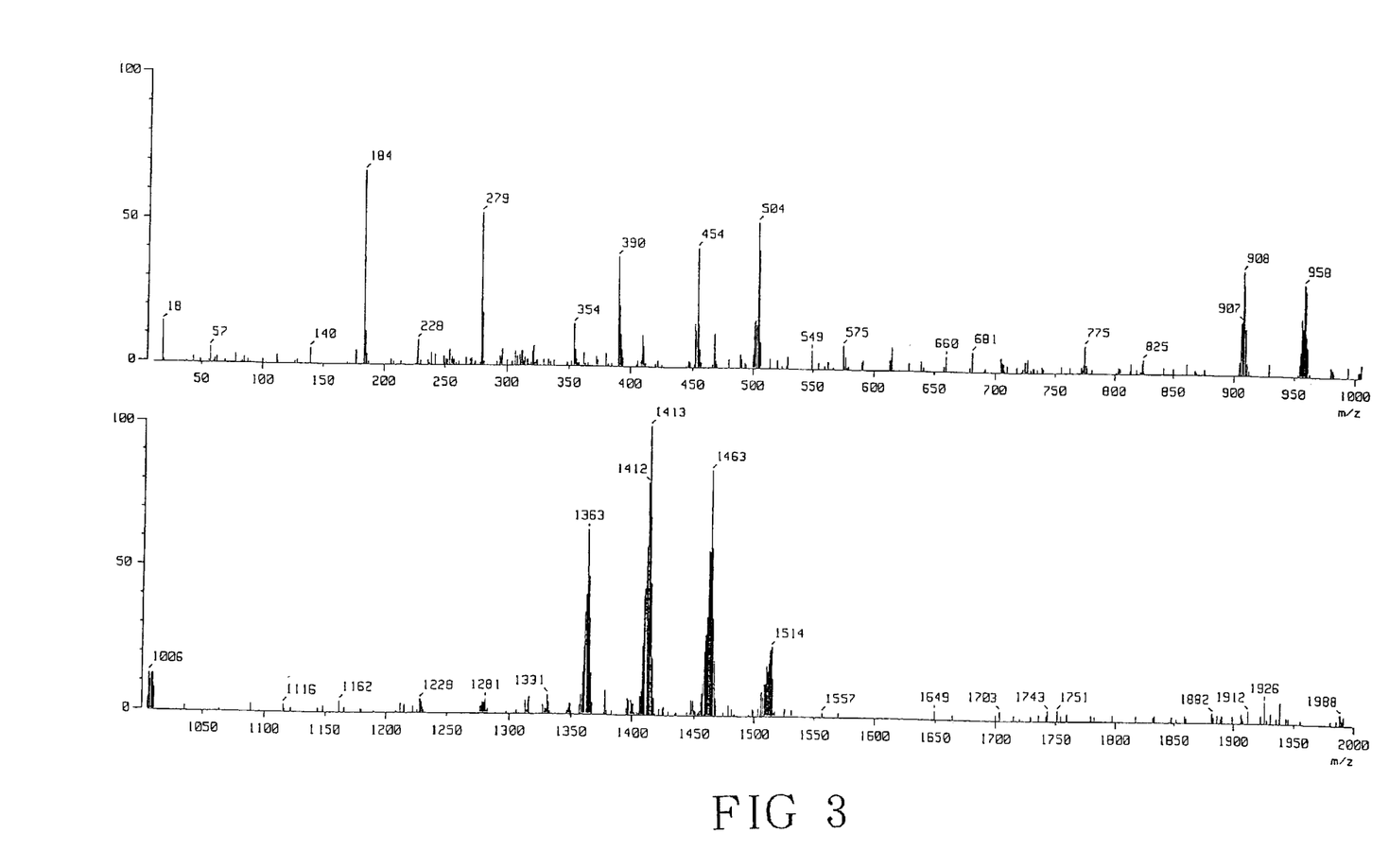
FIG. 3 shows the FD-MS chart of the second fraction, more particularly $(Ba_{0.003}Sr_{0.523})(dpm)_2$.

The FD-MS data of the second fraction, more particularly $(Ba_{0.477}Sr_{0.523})(dpm)_2$ are shown in FIG. 3.

The FD-MS list of the second fraction is shown in Table 4.

TABLE 4

FD-MS list of the second fraction
(Intensity has been normalized by taking m/z = 1413 as 100.)

| Ionic species | m/z | Intensity | Sum of intensities |
| --- | --- | --- | --- |
| $Sr(dpm)_2$ | 452 | 15.08 |  |
|  | 453 | 12.42 |  |
|  | 454 | 41.49 |  |
|  | 455 | 14.72 |  |
|  | 456 | 6.17 | 89.88 |
| $Bd(dpm)_2$ | 500 | 4.57 |  |
|  | 501 | 15.98 |  |
|  | 502 | 16.45 |  |
|  | 503 | 14.94 |  |

TABLE 4-continued

FD-MS list of the second fraction
(Intensity has been normalized by taking m/z = 1413 as 100.)

| Ionic species | m/z | Intensity | Sum of intensities |
|---|---|---|---|
|  | 504 | 50.61 |  |
|  | 505 | 40.90 |  |
|  | 506 | 8.78 | 152.23 |
| $Sr_2(dpm)_4$ | 905 | 4.41 |  |
|  | 906 | 18.13 |  |
|  | 907 | 18.62 |  |
|  | 908 | 36.17 |  |
|  | 909 | 31.29 |  |
|  | 910 | 15.93 |  |
|  | 911 | 4.06 | 128.61 |
| $SrBa(dpm)_4$ | 954 | 3.87 |  |
|  | 955 | 8.08 |  |
|  | 956 | 19.98 |  |
|  | 957 | 16.71 |  |
|  | 958 | 31.97 |  |
|  | 959 | 29.71 |  |
|  | 960 | 23.64 |  |
|  | 961 | 9.60 | 133.56 |
| $Ba_2(dpm)_4$ | 1004 | 1.95 |  |
|  | 1005 | 4.22 |  |
|  | 1006 | 12.67 |  |
|  | 1007 | 10.29 |  |
|  | 1008 | 12.19 |  |
|  | 1009 | 12.54 |  |
|  | 1010 | 7.77 | 61.63 |
| $Sr_3(dpm)_6$ | 1358 | 6.64 |  |
|  | 1359 | 14.22 |  |
|  | 1360 | 23.07 |  |
|  | 1361 | 34.83 |  |
|  | 1362 | 40.93 |  |
|  | 1363 | 63.47 |  |
|  | 1364 | 47.30 |  |
|  | 1365 | 32.79 |  |
|  | 1366 | 14.01 |  |
|  | 1367 | 3.90 | 281.16 |
| $Sr_2Ba(dpm)_6$ | 1406 | 6.33 |  |
|  | 1407 | 8.07 |  |
|  | 1408 | 23.42 |  |
|  | 1409 | 40.69 |  |
|  | 1410 | 43.30 |  |
|  | 1411 | 57.74 |  |
|  | 1412 | 80.09 |  |
|  | 1413 | 100.00 |  |
|  | 1414 | 68.46 |  |
|  | 1415 | 45.05 |  |
|  | 1416 | 19.33 |  |
|  | 1417 | 5.69 | 498.17 |
| $SrBa_2(dpm)_6$ | 1454 | 1.49 |  |
|  | 1455 | 4.65 |  |
|  | 1456 | 7.54 |  |
|  | 1457 | 10.72 |  |
|  | 1458 | 21.88 |  |
|  | 1459 | 27.60 |  |
|  | 1460 | 33.78 |  |
|  | 1461 | 56.55 |  |
|  | 1462 | 56.19 |  |
|  | 1463 | 84.74 |  |
|  | 1464 | 57.68 |  |
|  | 1465 | 33.24 |  |
|  | 1466 | 18.63 |  |
|  | 1467 | 5.81 | 420.50 |
| $Ba_3(dpm)_6$ | 1506 | 8.00 |  |
|  | 1507 | 6.14 |  |
|  | 1508 | 10.72 |  |
|  | 1509 | 10.87 |  |
|  | 1510 | 16.86 |  |
|  | 1511 | 15.05 |  |
|  | 1512 | 18.03 |  |
|  | 1513 | 22.47 |  |
|  | 1514 | 23.46 |  |
|  | 1515 | 12.68 | 144.28 |

FIG. 1 shows the main molecule of $Ba(dpm)_2$ was $Ba_3(dpm)_6$ at around the m/z of 1512 while Sr as the trace impurity was in the form of $Ba_2Sr(dpm)_6$ observed at around the m/z of 1462. FIG. 2 shows that the main molecule of $Sr(dpm)_2$ was $Sr_3(dpm)_6$ observed at around the m/z of 1363 while Ba as the trace impurity was in the form of $Ba_2Sr(dpm)_6$ observed at around the m/z of 1413. These compounds were both trimers as anticipated based on the results of the molecular weight determination. FIG. 3 and Table 4 indicate that the second fraction was a mixture of $Ba_2Sr(dpm)_6$ with $BaSr_2(dpm)_6$ observed respectively at around the m/z of 1463 and around the m/z of 1413. $Ba_2Sr(dpm)_6$ and $BaSr_2(dpm)_6$ are both novel compounds which are diketonate molecules of trimers composed of two different elements. They are the compounds of the present invention. These two novel compounds are indicated as $(Ba,Sr)_3(dpm)_6$.

The structures of these novel compounds $Ba_2Sr(dpm)_6$ and $BaSr_2(dpm)_6$ are still unknown. Supposing that they are in the most likely form of hexa dentate linear trimers, each compound has two molecular species consisting of three atoms, as follows:

$Ba_2Sr(dpm)_6$: Ba—Ba—Sr and Ba—Sr—Ba.
$BaSr_2(dpm)_6$: Ba—Sr—Sr and Sr—Ba—Sr.

The vapor pressures of these novel compounds are very close to each other, though seemingly not identical. Therefore, it can be thought that they can be regarded as substantially the same with each other as a CVD source.

The physical properties of $(Ba,Sr)_3(dpm)_6$ according to the present invention were measured. By way of example, use was made, as the samples for the measurement, of the above fractions $(Ba_{0.48}Sr_{0.52})(dpm)_2$.

(1) Melting Point

Each sample was introduced into a glass capillary and its melting point was measured with the naked eye:
first fraction: 160° C.
second fraction: 160° C.
third fraction: 160° C.

(2) Liquid Density
1.1 g/cm³(180° C.)

(3) Vapor Pressure
method: gas saturation method.

Porous ceramic grains were impregnated with a sample in a molten state and then packed into a glass cylinder. A carrier gas Ar was fed into the cylinder from the bottom thereof and Ar and the vaporized sample were introduced from the top into a cooling tube. After trapping, the Ba and Sr contents were analyzed. The measurement was effected under the total pressure of 10 Torr at 200° C. The vapor pressure in terms of a monomer was determined for convenience's sake.

Vapor pressure at 200° C. (in terms of monomer): 0.02 Torr.

The first, second and third fractions showed the same vapor pressure.

(4) Kinematic Viscosity

The kinematic viscosity of the second fraction was measured by using a glass capillary viscometer (Cannon-Fenske Model).
87.3 cSt (centistokes)/180° C.
44.9 cSt/200° C.
23.8 cSt/220° C.

(5) TG-DTA
Measurement conditions: sample weight: 16.53 mg
atmosphere: Ar 1 atm
temperature rise rate: 10.0 deg/min.

Figure 4:
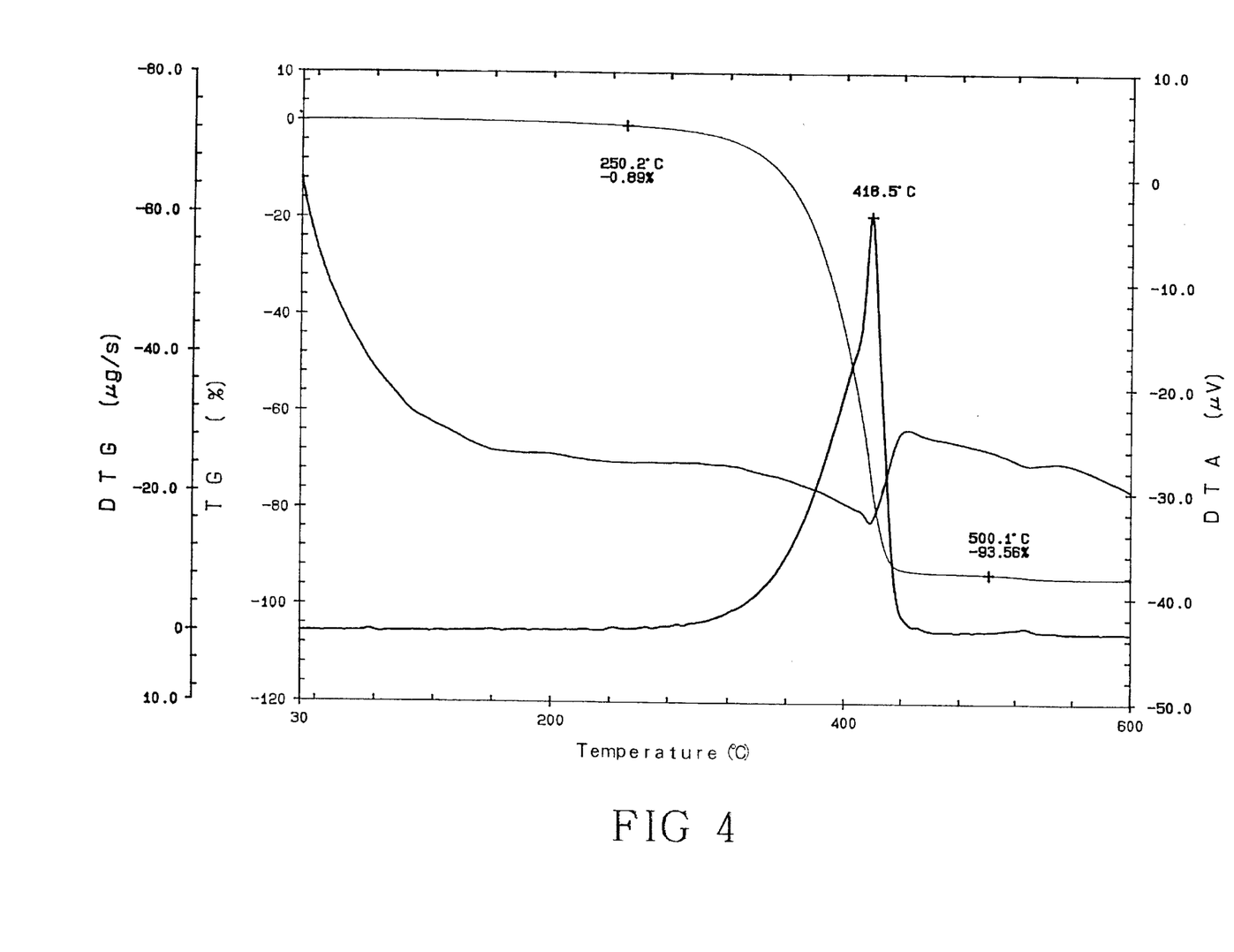
FIG. 4 shows the TG-DTA chart of the second fraction.

FIG. 4 shows the data of the second fraction. Other fractions gave similar results.

As FIG. 4 clearly shows, the weight loss in TG began at about 240° C. The weight loss reached 50% and 93% respectively at 400° C. and 440° C. No clear-cut melting point was observed in DTA. This is seemingly because the sample was a mixture of compounds having various structures.

(6) Solubility

Solubility in toluene (g/100 ml toluene, 20° C.):

first fraction: 13 second fraction: 15 third fraction: 20.

The solubility of each single component will be given below by way of reference:

$Ba(dpm)_2$: 2

$Sr(dpm)_2$: 145.

(7) Heat Stability 5 g of the second fraction was introduced into a SUS32 tube (Ar atmosphere) followed by sealing up. After keeping in an oil bath at 200° C. for 10 days, it was taken out therefrom and analyzed by TG-DTA. As a result, no change was observed.

The present invention further relates to processes for producing the compounds of the present invention at a high mass productivity.

The first process comprises reacting barium and strontium with a β-diketone in a solvent, removing the solvent and then purifying and recovering the product by high-vacuum distillation to thereby give barium strontium β-diketonate. It will suffice when the barium and strontium are supplied at a ratio corresponding to the target Ba:Sr ratio. As the solvent, it is preferable to use oxygen-free and dried hydrocarbons such as toluene. The reaction temperature is the boiling point of the solvent. That is, the reaction is effected under reflux. The reaction time varies depending on the surface areas and surface activities of the metals. In general, it ranges from several hours to several days. When specified amounts of the metals are consumed in the reaction, the solvent is removed and the product is purified and recovered by high-vacuum distillation. It is not desirable to effect purification by recrystallization, since the purified product is liable to be contaminated with solvent molecules, unreacted β-diketone and less volatile organic matters.

The second process comprises reacting barium with a β-diketone in a solution of strontium β-diketonate, removing the solvent and then purifying and recovering the product by high-vacuum distillation to thereby give barium strontium β-diketonate. As the solvent, it is preferable to use hydrocarbons such as toluene. The reaction temperature is the boiling point of the solvent. That is, the reaction is effected under reflux. The β-diketone is supplied preferably in excess at the equivalence point to the barium. Unless it is employed in excess, the reaction proceeds slowly and thus it takes a very long time to complete the reaction. The reaction time ranges from several hours to several tens of hours.

The third process comprises reacting strontium β-diketonate with barium β-diketonate optionally in a solvent, removing the solvent, if any, and then purifying and recovering the product by high-vacuum distillation to thereby give barium strontium β-diketonate. As the solvent, if employed, it is preferable to select toluene, etc. The reaction is effected at the boiling point of the solvent under reflux for one to several days. When no solvent is used, a strontium β-diketonate powder is mixed with a barium β-diketonate powder and then the resultant mixture is maintained at 220 to 230° C. for several hours to one day to thereby perform the reaction in a molten state.

The present invention further provides a process for producing barium strontium-containing oxide dielectric films by the chemical vapor deposition method which comprises bringing a heated substrate into contact with barium strontium β-diketonate.

Examples of the barium strontium-containing oxide dielectric films include BST films and SBN films. The Ba:Sr ratio of the feedstock barium strontium β-diketonate is determined depending on the Ba:Sr ratio of the desired film composition. Although the Ba:Sr ratio of the feedstock may be the same as that of the desired film composition, it should be somewhat modified in some cases depending on the CVD conditions.

The barium strontium β-diketonate to be used as the feedstock in the CVD method is in the form of a liquid, since it has been heated to 180 to 230° C. under reduced pressure. After bubbling a carrier gas into this liquid, it is combined with other oxide feedstock gas while maintaining at an appropriate temperature by heating so as to prevent the gas from condensation. Then the mixture is introduced into a CVD chamber, where it is mixed with an oxidative gas such as $O_2$ or $N_2O$ and thermally decomposed on a substrate heated to 500 to 700° C. to thereby give a composite oxide film.

As the second method of supply, use can be made of a supporting/evaporation system. In this system, the feedstock liquid is supported on porous ceramic grains by impregnation and then packed into a cylinder. After heating to 180 to 230° C., a carrier gas is fed into the layer. Then the saturated vapor of barium strontium β-diketonate is taken out and introduced into a CVD chamber. This supporting/evaporation system has an advantage that since the liquid is held in the pores and thus the vapor-liquid interfacial area is enlarged, the saturated vapor can be readily obtained while gas pressure loss is lessened. It is preferred that the source bubbler and the supporting/evaporation cylinder are operated under a pressure as low as 10 to 150 Torr. This is because a number of feedstock materials can be evaporated together at a low carrier gas flow rate and a trace amount of gas impurities formed by thermal decomposition, etc. can be discharged from the cylinder thereby, thus minimizing the degradation of the source.

As the third method of supply, use can be made of a system which comprises dissolving the barium strontium β-diketonate feedstock in THF, etc. followed by flash evaporation.

In the case of a BST film, a gas such as $Ti(OiPr)_4$ or $Ti(OiPr)_2(dpm)_2$ is used as a $TiO_2$ source. Since the Ba:Sr ratio of the film is determined depending on the Ba:Sr ratio of the barium strontium β-diketonate source, the appropriate (Ba+Sr)/Ti ratio of the film may be achieved by regulating the gas supply from the $TiO_2$ source.

In general, the thermal CVD is effected at a substrate temperature of 500 to 700° C. under a pressure of 0.1 to 10 Torr with the use of $O_2$ or $N_2O$ as the oxidative gas.

In addition to the thermal CVD method, use may be made of the ECR-plasma CVD method, the laser CVD method, etc. in the present invention.

In the case of an SBN film, a gas such as $Nb(OEt)_5$ is used as an $Nb_2O_5$ source. Since the Ba:Sr ratio of the film is determined depending on the Ba:Sr ratio of the barium strontium β-diketonate source, the appropriate (Ba+Sr)/Nb ratio of the film may be achieved by regulating the gas supply from the $Nb_2O_5$ source.

In general, the heat CVD is effected at a substrate temperature of 500 to 700° C. under a pressure of 1 to 100 Torr with the use of $O_2$ or $N_2O$ as the oxidative gas.

EXAMPLE 1
Production of Barium Strontium β-diketonate $(Ba_{0.48}Sr_{0.52})$ $(dpm)_2$ A 500 ml four-necked flask provided with a reflux condenser, a thermometer and stirring blades was vacuum purged with argon. Then 350 ml of toluene was fed thereinto followed by the supply of 40.3 g (89 mmol) of $Sr(dpm)_2$, 65.6 g (356 mmol) of dipivaloylmethane dpmH and 12.2 g (89 mmol) of a metallic barium piece. The resultant mixture was heated with stirring. When it reacted under reflux for 8 hours, the metal piece disappeared. Next, the solvent and the unreacted dpmH components were distilled off under reduced pressure. The residue was further treated at 170° C. under 0.05 Torr to thereby distill off the dissolved dpmH remaining in a small amount. A 65 g portion of the residue was transferred to a high-vacuum distillation apparatus, where it was distilled by heating at an oil bath temperature of 220° C. under 0.02 Torr to give 19.5 g of the first fraction, 21.7 g of the second fraction and 19.2 g of the third fraction. These three fraction were each in the form of a pale yellow solid at room temperature. The identification thereof and the measurement of their physical properties were performed by the methods described above.

EXAMPLE 2
Production of Barium Strontium β-diketonate $(Ba_{0.49}Sr_{0.51})$ $(dpm)_2$ A 500 ml four-necked flask provided with a reflux condenser, a thermometer and stirring blades was vacuum purged with argon. Then 400 ml of toluene was fed thereinto followed by the supply of 14.94 g (29.7 mmol) of $Ba(dpm)_2$ and 13.80 g (30.4 mmol) of $Sr(dpm)_2$. The resultant mixture was stirred at 20° C. for 8 hours but the $Ba(dpm)_2$ was not dissolved at all. Next, the mixture was maintained under the reflux of toluene for 24 hours. As a result, the reactants were completely dissolved and turned slightly yellow and transparent. After distilling off the solvent, the residue was subjected to high-vacuum distillation at an oil bath temperature of 220° C. under 0.02 Torr to give 25 g of a pale yellow distillate, which was $(Ba_{0.49}Sr_{0.51})(dpm)_2$ with a Ba:Sr ratio of 0.49:0.51, having a melting point of 160° C. and TG-DTA data similar to those given in FIG. 4.

EXAMPLE 3
Production of Barium Strontium β-diketonate $(Ba_{0.49}Sr_{0.51})$ $(dpm)_2$ A high-vacuum distillation still made of Pyrex was vacuum purged with argon. Then 24.60 g (48.8 mmol) of $Ba(dpm)_2$ and 22.75 g (50.1 mmol) of $Sr(dpm)_2$ were supplied thereinto. The still was heated in an oil bath at 220° C. for 6 hours to give a yellow and transparent liquid. Next, it was subjected to high-vacuum distillation at an oil bath temperature of 220° C. under 0.02 Torr to give 42 g of a pale yellow distillate, which was $(Ba_{0.49}Sr_{0.51})(dpm)_2$ with a Ba:Sr ratio of 0.49:0.51, having a melting point of 160° C. and TG-DTA data similar to those given in FIG. 4.

EXAMPLE 4
Production of Barium Strontium β-diketonate $(Ba_{0.51}Sr_{0.49})$ $(dpm)_2$ A 500 ml four-necked flask provided with a reflux condenser, a thermometer and stirring blades was vacuum purged with argon. Then 400 ml of toluene was fed thereinto followed by the successive supply of 38.0 g (206 mmol) of dipivaloylmethane dpmH and 3.80 g (27.7 mmol) of a Ba piece and 2.33 g (26.6 mmol) of an Sr piece. After heating the resultant mixture under reflux, the metal pieces disappeared. Next, the solvent and the unreacted dpmH were distilled off under reduced pressure. The residue was further subjected to high-vacuum distillation at an oil bath temperature of 220° C. under 0.02 Torr to give 24 g of a pale yellow distillate which was $(Ba_{0.51},Sr_{0.49})(dpm)_2$ with a Ba:Sr ratio of 0.51:0.49, and showing TG-DTA data similar to those given in FIG. 4.

EXAMPLE 5
Production of BST Film by the CVD Method

During the embodiment of the CVD method, the whole feedstock container and thermal decomposition reactor systems were maintained under 10 Torr.

A feedstock container 1 packed with 40 g of $(Ba_{0.49}Sr_{0.51})(dpm)_2$ was introduced into a thermostatic chamber at 200° C. and a carrier gas Ar was bubbled thereinto at 20 sccm. $(Ba_{0.49}Sr_{0.51})(dpm)_2$ evaporated with it and the mixture was fed into the thermal decomposition reactor via a gas mixer. Separately, 30 g of $Ti(OiPr)_2$ was supported on porous ceramic grains, which were then packed into another feedstock container 2. Then it was introduced into a thermostatic chamber at 125° C. and a carrier gas Ar was supplied thereinto at 30 sccm. $Ti(OiPr)_4$ sublimated together with this gas and the mixture was fed into the thermal decomposition reactor via a gas mixer. At the same time, an oxygen gas was introduced into the thermal decomposition reactor at 50 sccm. The thermal decomposition reactor had been provided therein with a $Pt/SiO_2/Si$ substrate heated to 550° C. The $(Ba_{0.49}Sr_{0.51})(dpm)_2$ and $Ti(OiPr)_2(dpm)_2$ underwent oxidative decomposition on this substrate and thus a BST film of 60 nm thickness was formed after 20 minutes. The result of XRD analysis indicated that this film had a perovskite structure. When this film was dissolved and the metal contents were analyzed by ICP emission spectroscopy, it was found out that the Ba:Sr:Ti ratio was 0.49:0.51:1.02.

EXAMPLE 6
Production of SBN Film by the CVD Method

During the embodiment of the CVD method, the whole feedstock container and thermal decomposition reactor systems were maintained under 10 Torr.

A feedstock container 1 packed with 40 g of $(Ba_{0.49}Sr_{0.51})(dpm)_2$ was introduced into a thermostatic chamber at 210° C. and a carrier gas Ar was bubbled thereinto at 20 sccm. $(Ba_{0.49}Sr_{0.51})(dpm)_2$ evaporated with it and the mixture was fed into the thermal decomposition reactor via a gas mixer. Separately, another feedstock container 2 packed with 40 g of $Nb(OEt)_5$ was introduced into a thermostatic chamber at 125° C. and a carrier gas Ar was supplied thereinto at 20 sccm. $Nb(OEt)_5$ evaporated with it and the mixture was fed into the thermal decomposition reactor via a gas mixer. At the same time, an oxygen gas was introduced into the thermal decomposition reactor at 40 sccm. The thermal decomposition reactor had been provided therein with a quartz substrate heated to 600° C. The $(Ba_{0.49}Sr_{0.51})(dpm)_2$ and $Nb(OEt)_5$ underwent oxidative decomposition on this substrate and thus an SBN film of 80 nm thickness was formed after 20 minutes. The result of XRD analysis indicated that this film had a tetragonal tungsten bronze structure. When this film was dissolved and the metal contents were analyzed by ICP emission spectroscopy, it was found out that the Ba:Sr:Nb ratio was 0.49:0.51:2.07.

Because of having a melting point of 160° C., being in the form of a liquid and having enough pressure at 200° C., the barium strontium β-diketonates, $[Ba_2Sr(dpm)_6$ and $BaSr_2(dpm)_6]$ according to the present invention can be quantitatively supplied by gas bubbling or by evaporation from a porous carrier as a feedstock in the CVD method while maintaining a constant Ba/Sr ratio. Thus, barium strontium-containing oxide dielectric films can be produced at a high reproducibility by thermal decomposition on a substrate in an oxidative atmosphere.

What is claimed is:

1. Barium strontium β-diketonate.

2. Barium strontium dipivaloylmethanate.

3. A process for producing barium strontium β-diketonates which comprises reacting barium and strontium with β-diketone in a solvent, removing the solvent and then purifying and recovering the product by high-vacuum distillation.

4. A process for producing barium strontium β-diketonates which comprises reacting barium with β-diketone in a solution of strontium β-diketonate, removing the solvent and then purifying and recovering the product by high-vacuum distillation.

5. A process for producing barium strontium β-diketonates which comprises reacting strontium β-diketonate with barium β-diketonate optionally in a solvent, removing the solvent and then purifying and recovering the product by high-vacuum distillation.

* * * * *